United States Patent
Panse et al.

(10) Patent No.: US 11,740,757 B2
(45) Date of Patent: *Aug. 29, 2023

(54) VIRTUAL COVER FOR USER INTERACTION IN AUGMENTED REALITY

(71) Applicant: KONINKLIJKE PHILIPS N.V., Eindhoven (NL)

(72) Inventors: Ashish Panse, Burlington, MA (US); Molly Lara Flexman, Melrose, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 17/743,629

(22) Filed: May 13, 2022

(65) Prior Publication Data

US 2022/0276764 A1 Sep. 1, 2022

Related U.S. Application Data

(63) Continuation of application No. 16/613,499, filed as application No. PCT/EP2018/061947 on May 9, 2018, now Pat. No. 11,334,213.

(Continued)

(51) Int. Cl.
*G06F 3/04815* (2022.01)
*G06F 3/01* (2006.01)
(Continued)

(52) U.S. Cl.
CPC .......... *G06F 3/04815* (2013.01); *G06F 3/012* (2013.01); *G06F 3/013* (2013.01);
(Continued)

(58) Field of Classification Search
CPC ...... G06F 3/04815; G06F 3/012; G06F 3/013; G06F 3/017; G06F 3/167; G06T 19/006
See application file for complete search history.

(56) References Cited

U.S. PATENT DOCUMENTS 9,152,309 B1 10/2015 Arrehn
2012/0013550 A1* 1/2012 Martinoli ............ G06F 3/04886
345/173

(Continued)

FOREIGN PATENT DOCUMENTS

JP 2013232062 A 11/2013

OTHER PUBLICATIONS

Nivedha Nivi et al., Enhancing user Experience through Physical Interaction in Handheld Augmented Reality, Jan. 1, 2015, IEEE Xplore, pp. 1-7 (Year: 2015).*

(Continued)

*Primary Examiner* — Tam T Tran

(57) ABSTRACT

A controller for augmenting reality in a three-dimensional (3D) space includes a memory that stores instructions; and a processor that executes the instructions. The controller controls a display system configured to present virtual objects in the 3D space. When executed by the processor, the instructions cause the controller to perform a process. The process includes detecting a first action by a user relative to an object or a virtual object in the 3D space. The process also includes selectively enabling or disabling a virtual operation member based on detecting the first action between the user and the object or virtual object in the 3D space. The virtual operational member is configured, when operated, to control operation of a machine in the 3D space.

20 Claims, 10 Drawing Sheets

Related U.S. Application Data

(60) Provisional application No. 62/506,895, filed on May 16, 2017.

(51) Int. Cl.
  *G06F 3/16* (2006.01)
  *G06T 19/00* (2011.01)

(52) U.S. Cl.
  CPC .............. *G06F 3/017* (2013.01); *G06F 3/167* (2013.01); *G06T 19/006* (2013.01)

(56) References Cited

U.S. PATENT DOCUMENTS

| | | | |
|---|---|---|---|
| 2012/0249416 A1* | 10/2012 | Maciocci | G06F 3/011 345/156 |
| 2013/0050069 A1* | 2/2013 | Ota | G06F 3/0304 345/156 |
| 2014/0266983 A1 | 9/2014 | Christensen | |
| 2015/0227222 A1 | 8/2015 | Sako | |
| 2016/0191887 A1 | 6/2016 | Casas | |
| 2016/0217614 A1* | 7/2016 | Kraver | G02B 27/017 |
| 2016/0313902 A1 | 10/2016 | Hill | |
| 2017/0076503 A1* | 3/2017 | Tamaoki | G06F 3/017 |
| 2018/0232506 A1* | 8/2018 | Kumar | G06V 40/13 |

OTHER PUBLICATIONS

Ajune Wanis Ismail et al., Multi-user Interaction in Collaborative Augmented Reality for Urban Simulation, Dec. 1, 2009, IEEE Computer Society, pp. 309-314 (Year: 2009).*

PCT/EP2018/061947 ISR & WO, Jul. 5, 2018 16 Page Document.

Li, Hanchuan e tal IDCam: Precise Item Identification for AR Enhanced Object Interactions, Apr. 2019, IEEE International Conf. on RFID, pp. 1-7.

Figueiredo, Lucas Silva et al Prepose: Privacy, Security, and Reliability for Gesture-Based P:rogramming, 2016, IEEE Computer Society, pp. 122-137.

* cited by examiner

VIRTUAL COVER FOR USER INTERACTION IN AUGMENTED REALITY

CROSS-REFERENCE TO PRIOR APPLICATIONS

This application is a Continuation of application Ser. No. 16/613,499, filed on Nov. 14, 2019, which is the U.S. National Phase application under 35 U.S.C. § 371 of International Application No. PCT/EP2018/061947, filed on May 9, 2018, which claims the benefit of U.S. Provisional Patent Application Ser. No. 62/506,895, filed May 16, 2017. These applications are hereby incorporated by reference herein.

BACKGROUND

Medical procedures such as interventional procedures use physical equipment that is controlled using physical operation members such as buttons, dials, levers, handles and similar mechanisms for turning equipment on and off and changing settings.

Augmented reality generally refers to when a live image stream is supplemented with additional computer-generated information. The live image stream can be via the eye, cameras or communications devices such as smart phones and tables. The live image stream is augmented via display to the user via glasses, contact lenses, projections or on the communications devices. Current augmented reality systems can sense and respond to a variety of user actions including gesture recognition, head tracking, eye tracking, and voice recognition.

As augmented reality is implemented in medical settings, virtual operation members will likely be used to control physical equipment. In the same way that inadvertent operation of physical operation members is dangerous, inadvertent operation of virtual operation members will also be dangerous.

SUMMARY

According to an aspect of the present disclosure, a controller for augmenting reality in a three-dimensional (3D) space includes a memory that stores instructions; and a processor that executes the instructions. The controller controls a display system configured to present virtual objects in the 3D space. When executed by the processor, the instructions cause the controller to perform a process. The process includes detecting a first action by a user relative to an object or a virtual object in the 3D space. The process also includes selectively enabling or disabling a virtual operation member based on detecting the first action between the user and the object or virtual object in the 3D space. The virtual operational member is configured, when operated, to control operation of a machine in the 3D space.

According to another aspect of the present disclosure, a method for controlling features in a 3D space with augmented reality includes controlling a display system configured to present virtual objects in the 3D space. The method also includes detecting a first action by a user relative to an object or a virtual object in the 3D space. The method further includes selectively enabling or disabling a virtual operation member based on detecting the first action between the user and the object or virtual object in the 3D space. The virtual operational member is configured, when operated, to control operation of a machine in the 3D space.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1A:
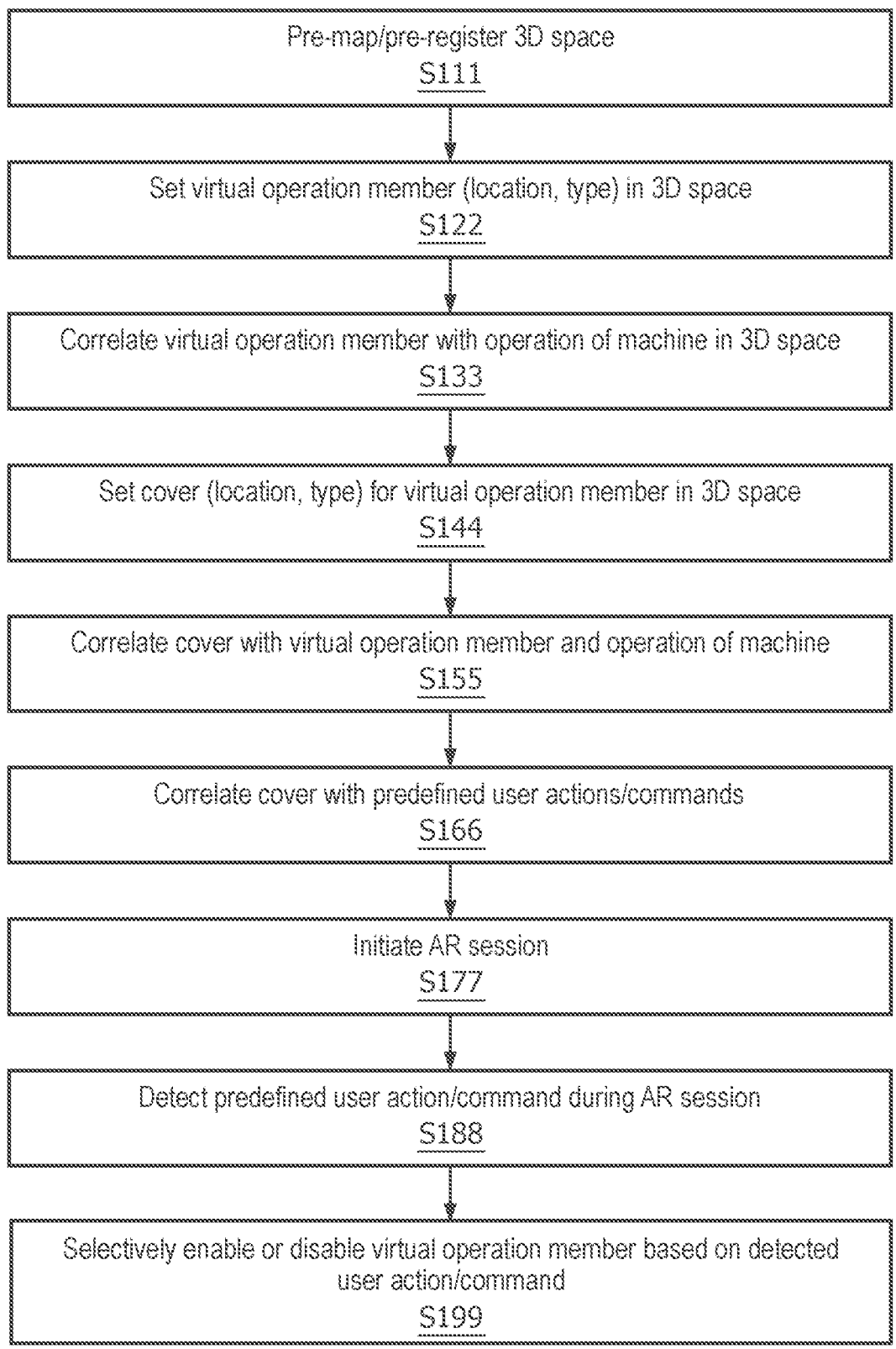
FIG. 1A illustrates a process for a virtual cover for user interaction in augmented reality, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing specific embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprise", and/or "comprising," and/or similar terms when used in this specification, specify the presence of stated features, elements, and/or components, but do not preclude the presence or addition of one or more other features, elements, components, and/or groups thereof. As used herein, the term "and/or" includes all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted to not obscure the description of the example embodiments. Such methods and apparatuses are within the scope of the present disclosure.

FIG. 1A illustrates a process for a virtual cover for user interaction in augmented reality, in accordance with a representative embodiment. The process shown in FIG. 1A may be representative of an overall process leading to selectively enabling or disabling a virtual operation member based on detected user actions or commands. As described herein, a virtual operation member may be a virtual button, virtual dial, virtual lever, virtual handle, or other virtual member that is visible using software that generates the virtual member as augmented reality in a 3D space. The virtual operation member can be specifically correlated with an operation of a machine, such as medical equipment. In other words, a user interacting with the virtual operation member can operate machinery.

Control as described herein is not limited to any particular type of machine, or even a machine at all. Rather, control via a virtual operation member can be of machines, settings, information, and other forms of items and information that can be controlled such as by turning on and off. Examples include images on a screen, a pointer, features such as playing music, and so on. A variety of examples of controllable items and information are set forth below following the description of FIGS. 1A and 1B.

Additionally, control may include both enabling and disabling of individual controllable items and information, or groups of all or subsets of all controllable items and information. For example, a virtual operation member may be an emergency control to immediately display a designated set of information from a set of electronic sources monitoring a patient when the patient's vital signs deteriorate quickly. The emergency control may be quickly enabled and activated using, for example a coded command or command sequence. Of course, master controls for all or subsets of all controllable items and information are not limited to emergencies, and may be applied, for example when a 3D space is shutting down after a session or at other times.

The process in FIG. 1A starts with pre-mapping/pre-registering a 3D space at S111. The 3D space may be, for example, an operating room or other enclosed space that will be used during an augmented reality session. The virtual operation member as described herein occupies a portion of the 3D space. The 3D space may be mapped before a session in which augmented reality is provided, so the mapping at S111 is pre-mapping in a sense. The mapping may be performed by visually capturing all physical parameters of the 3D space and any physical items (e.g., furniture, equipment) in the 3D space. The 3D space may also be registered before the session in which augmented reality is provided, so the registering at S111 is also pre-registering in a sense. The registering may be performed by labelling each physical parameter of the 3D space and each physical item in the 3D space.

A computer program used to map and register the 3D space may be linked to a library of characteristics of physical parameters and physical items. A library of characteristics can be used to facilitate registering by linking any physical parameter or physical item identified in the mapping with a predetermined description. The mapping and registering are performed so that all areas in the 3D space in which virtual objects can be placed can be identified.

The mapping and registering can also be performed at the time of the AR session. For example, although the mapping at S11 is described above as pre-mapping, a 3D space can also be dynamically mapped after an augmented reality session begins, such as by using the sensors of augmented reality devices to collect parameters of a 3D space and then using image recognition to register the physical parameters and physical items in the 3D space.

At S122, a virtual operation member is set in the 3D space. As noted above, the virtual operation member may be representative of a physical operation member used to control a machine. For example, a type of the virtual operation member may be retrieved from a library that specifies different types and appearances of buttons, dials, levers, handles and similar forms of mechanical or electro-mechanical inputs. The location of the virtual operation member may also be set in the 3D space, such as by virtually moving the virtual operation member with gestures to place the virtual operation member at a specific location in the 3D space that is mapped. Of course, the location of the virtual operation member can also be manipulated using, for example, a mouse, a joystick, a touchscreen, a roll pad, or other forms of inputs known for computers and electronic devices.

At S133, the virtual operation member is correlated with a specific operation of a machine in the 3D space. For instance, the virtual operation member may be correlated with turning an X-Ray machine of or off, or with capturing an image or reading using the machine. The operation of the virtual operation member may be correlated at several levels, including in the software that captures and interprets the user actions or commands relative to the virtual operation member, and software that controls operation of the machine.

At S144, a cover for the virtual operation member is set in the 3D space. The may correspond to a type of cover selected from a library. A cover may be given the appearance of a physical cover, such as a cover for a touchpad that hides buttons on the touchpad from view so they cannot be manipulated. In the same way, the cover set at S144 may be used to hide the virtual operation member from view in augmented reality. The location of the cover may be set in the 3D space, such as by virtually moving the cover with gestures to place the cover at a specific location in the 3D space that is mapped. The location of the virtual operation member can also be manipulated using, for example, a mouse, a joystick, a touchscreen, a roll pad, or other forms of inputs known for computers and electronic devices.

At S155, the cover is correlated with the virtual operation member and the operation of the machine. That is, the cover may be logically correlated in augmented reality software to hide or unhide the virtual operation member in the augmented reality when manipulated. Operation of the cover may also be correlated in the software that controls operation of the machine, such as by disabling operation of the machine when the cover is "over" the virtual operation member. In this way, the virtual operation member cannot be unintentionally manipulated since the virtual operation member will not be visible in the augmented reality space that includes the virtual operation member and the cover At S166, the cover is correlated with predefined user actions and commands. The predefined user actions and commands are specific actions and commands that will be interpreted as instructions to activate the cover or deactivate the cover, such as by moving the cover over the virtual operation member. For example, a swiping action from left to right on or immediately around the cover may be interpreted to "open" the cover when closed, and a swiping action from right to left may be interpreted to "close" the cover when open. The augmented reality software may also interpret verbal instructions such as "open the cover" or "close the cover" to correspond to specific actions to take relative to the cover.

At S177 an augmented reality session is initiated. An augmented reality session may be considered to start when a first subject wearing a head-mountable device enters a 3D space. Moreover, multiple augmented reality sessions may take place simultaneously, wherein each of multiple different subjects wearing head-mountable devices individually enters the 3D space. The head-mountable devices may be pre-programmed or preauthorized to access the portion of the 3D space which is occupied by the virtual operation member and the cover. For example, augmented reality sessions may correspond to a medical intervention occurring in a pre-mapped operating room serving as the 3D space, and each subject authorized to access the virtual reality object may access information displayed via virtual reality during the medical intervention.

At S188, one of the predefined user actions or commands from S166 may be detected, and at S199 the virtual operation member may be selectively enabled or disabled based on the detected user action or command. That is a predefined action to open a virtual cover may be detected at S188, and the augmented reality software and the software used to operate the machine may both then accept commands to operate the machine using the virtual operation member.

The virtual operation member and the cover may be visible via augmented reality using head-mountable devices. However, augmented reality is not restricted only to head-mountable devices. Rather, head-mountable devices are readily explained in the context of a 3D space such as an operating room and are used as examples for convenience herein. The virtual operation member and the cover occupying part of a 3D space as augmented reality may be displayed to any authorized subject with a view of the 3D space that includes the virtual operation member and the cover. Alternatively, the virtual operation member and the cover may only be visible to one or a subset of specifies users who would be authorized to manually operate the machinery correlated with the virtual operation member and the cover. For example, even a remote user watching the 3D space via a camera may have access to the virtual operation member when the remote user is so authorized. In addition to head-mountable devices, users with access to a virtual operation member and a cover may use projected images, transparent heads-up displays, and other forms of augmented reality devices.

Figure 1B:
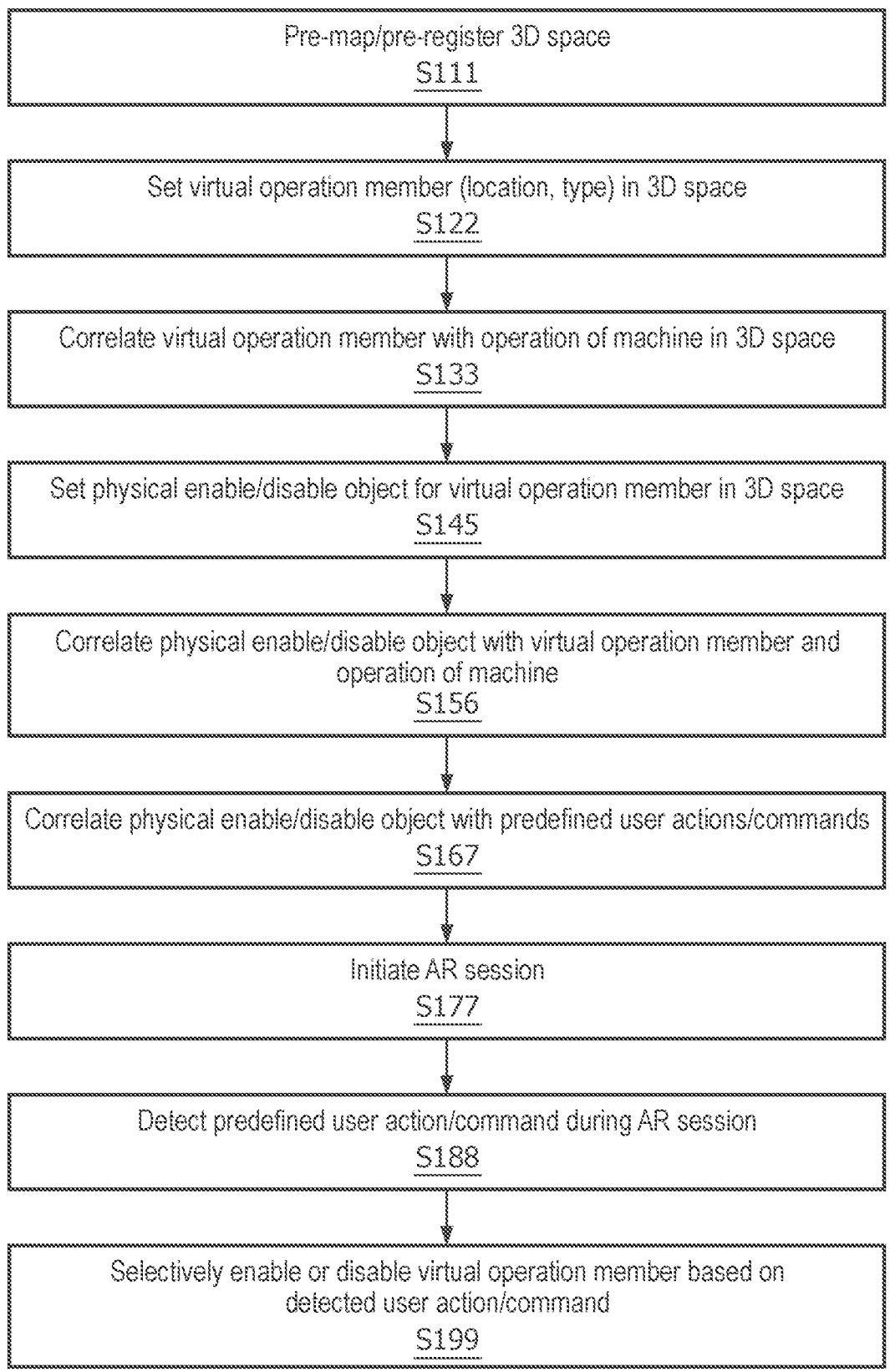
FIG. 1B illustrates another process for a virtual cover for user interaction in augmented reality, in accordance with a representative embodiment.

FIG. 1B illustrates another process for a virtual cover for user interaction in augmented reality, in accordance with a representative embodiment. The process shown in FIG. 1B may again be representative of an overall process leading to selectively enabling or disabling a virtual operation member based on detected user actions or commands. Several of the activities shown in FIG. 1B are the same as shown for FIG. 1A, and detailed explanations are therefore not repeated.

The process in FIG. 1B starts with pre-mapping/pre-registering a 3D space at S111, and includes setting a virtual operation member in 3D space at S122 and correlating the virtual operation member with operation of a machine in the 3D space at S133.

At S145, a physical enable/disable object is set for the virtual operation member in 3D space. For example, a foot pedal next to or under a bed in the 3D space may be correlated with enabling or disabling the virtual operation member. In this way, and as an example, a user may be required to depress the foot pedal to view the virtual operation member in the augmented reality, and then interact with the virtual operation member in the augmented reality space to operate the machinery in the 3d space. An example of how this can be used to provide a safeguard is for X-ray equipment, where a user must combine a physical action with an interaction in augmented reality to uncover an "on" button and then virtually interact with the "on" button to operate the X-ray equipment.

At S156, the physical enable/disable object is correlated with the virtual operation member and operation of the machine. That is, the physical enable/disable object may be logically correlated in augmented reality software to hide or unhide the virtual operation member in the augmented reality when manipulated. Operation of the physical enable/disable object may also be correlated in the software that controls operation of the machine, such as by disabling operation of the machine when the physical enable/disable member is not depressed. In this way, the virtual operation member cannot be unintentionally manipulated since the virtual operation member will not be visible in the augmented reality space that includes the virtual operation member.

At S167, the physical enable/disable object is correlated with predefined user actions and commands. The predefined user actions and commands are specific actions and commands that will be interpreted as instructions to activate the physical enable/disable, and here are limited compared to the virtual cover used in FIG. 1A. For example, a foot pedal may only have 2 or possible readings of on and off.

At S177 an augmented reality session is initiated, and at S188 the predefined user action or command is detected during the augmented reality session. At S199, the virtual operation member is selectively enabled or disabled based on the detected user action or command. For example, as noted above, a user pressing a foot pedal may activate or deactivate the virtual operation member used to operate a machine.

In embodiments herein, control is not limited to operation of a particular type of machine or even a machine at all. Rather, control may include operation of an X-ray machine, an ultrasound machine, robots (e.g., surgical robots), electromechanical environmental controls for a room, and a variety of types of medical equipment, as examples. However, control may also be control of virtual information and other types of devices that might not satisfy a particular definition of a machine. Examples of machines and other mechanisms that can be controlled include:

X-ray machines:
Physical positioning of a c-arm, table.
X-ray configuration, such as dose levels, wedges, collimation.
Image display, such as bringing up different images for review,
masking of images, annotating.
Ultrasound machines:
Image acquisition parameters, such as focus, depth, gain.
Display parameters, such as rotating an image around.
Robots, such as catheter robots, surgical robots.
Electromechanical environmental or room controls.
Lights on/off.
Sound, such as music, audio communication to a control room.
Timers on/off.
Annotation on/off.
Voice or camera recording on/off.
Other equipment, such as IVUS, FFR, patient vitals, anesthesia equipment.
Virtual information:
Controls of what to show, such as which screens and where.
Pointers or selectors for virtual information, such as placing landmarks,
selecting certain objects, annotating images/models.
Interacting with a model (causing it to rotate, get bigger/smaller, etc.).

Figure 2A:
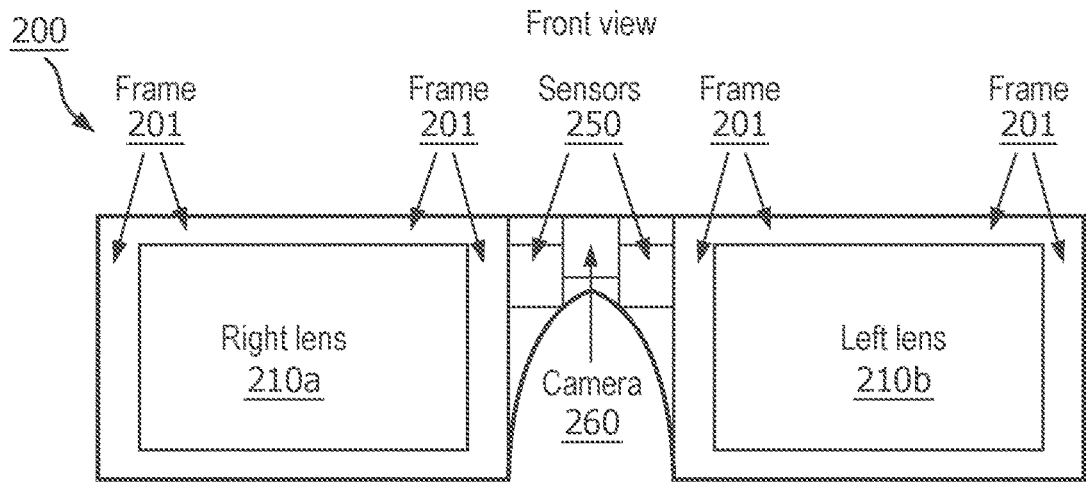
FIG. 2A illustrates a front view of a head-mountable device for a virtual cover for user interaction in augmented reality, in accordance with an aspect of the present disclosure.

FIG. 2A illustrates a front view of a head-mountable device for a virtual cover for user interaction in augmented reality, in accordance with an aspect of the present disclosure. In FIG. 2a, head-mountable device 200 includes a frame 201 in which a right lens 210a and a left lens 210b are separately enclosed. Sensors 250, camera 260 are representative of electronic components integrated in and/or on the frame 201.

As explained herein, the left lens 210b and the right lens 210a may each be provided in front of, or behind, a transparent optical display. Transparent optical displays may be controlled by image processors to generate virtual objects that are superimposed in the field of view of the subject wearing the head-mountable device 200. Alternatively, the left lens 210b and the right lens 210a may each be provided in front of mirrors that reflect light from a projector into the eyes of the subject wearing the head-mountable device 200. The effect of mirrors is the same as the effect of using transparent optical displays in that virtual objects are superimposed in the field of view of the subject wearing the head-mountable device 200.

The camera 260 faces forward to provide a forward view from the viewpoint of the subject wearing the head-mountable device 200. The camera 260 may be representative of multiple cameras, including cameras of different types (RBG, grayscale, depth sensing cameras, IR cameras, spectral cameras). The sensors 250 sense aspects of the environment around the head-mountable device 200.

The sensors 250 may include, for example, accelerometers, gyroscopes, resistive sensors, current sensors, piezoelectric sensors, voltage sensors, capacitive sensors, global positioning satellite receivers, compasses, altimeters, cameras, rangefinders, microphones, thermometers, chemical sensors, moisture sensors, and so on. The sensors 250 sense movement of the subject wearing the head-mountable device 200, such as when and by how much the subject tilts or swivels their head. The sensors 250 also sense environmental conditions of the environment around the head-mountable device 200, such as temperature and humidity, lighting conditions, and more. As explained below relative to FIG. 2C, cameras 270a, 270b may also be provided as sensors to track eye movements of the operator.

Figure 2B:
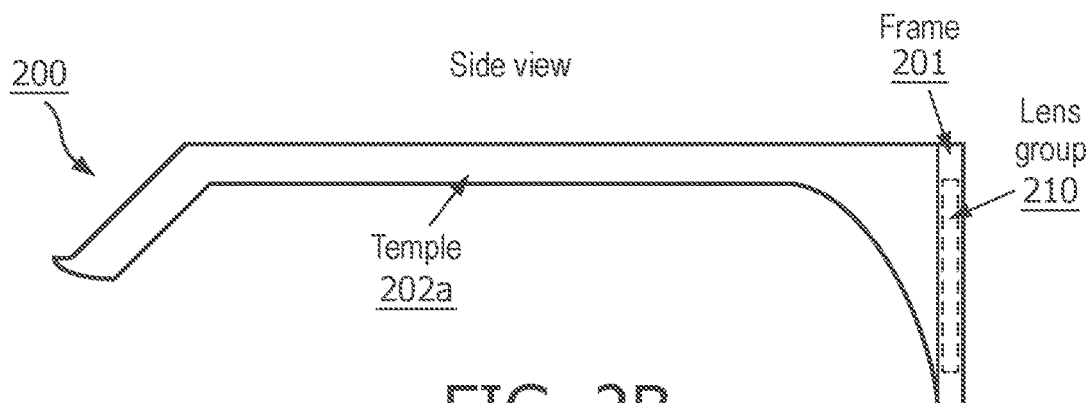
FIG. 2B illustrates a side view of a head-mountable device for a virtual cover for user interaction in augmented reality, in accordance with an aspect of the present disclosure.

FIG. 2B illustrates a side view of a head-mountable device for a virtual cover for user interaction in augmented reality, in accordance with an aspect of the present disclosure. In FIG. 2B, a right temple 202a is shown extending from a lens group 210 enclosed in the frame 201. The lens group 210 includes the right lens 210a and left lens 210b as shown in FIG. 2A.

The right temple 202a is for the right side of the head of the subject wearing the head-mountable device 200. A left temple 202b is provided for the left side of the head of the subject wearing the head-mountable device 200, as is explained below with respect to FIG. 2C. The right temple 202a is used to hold the head-mountable device 200 over an ear of the subject wearing the head-mountable device 200. As shown in FIG. 2A, the middle portion of the front of the head-mountable device 200 can also be balanced on a nose of the subject wearing the head-mountable device 200.

Figure 2C:
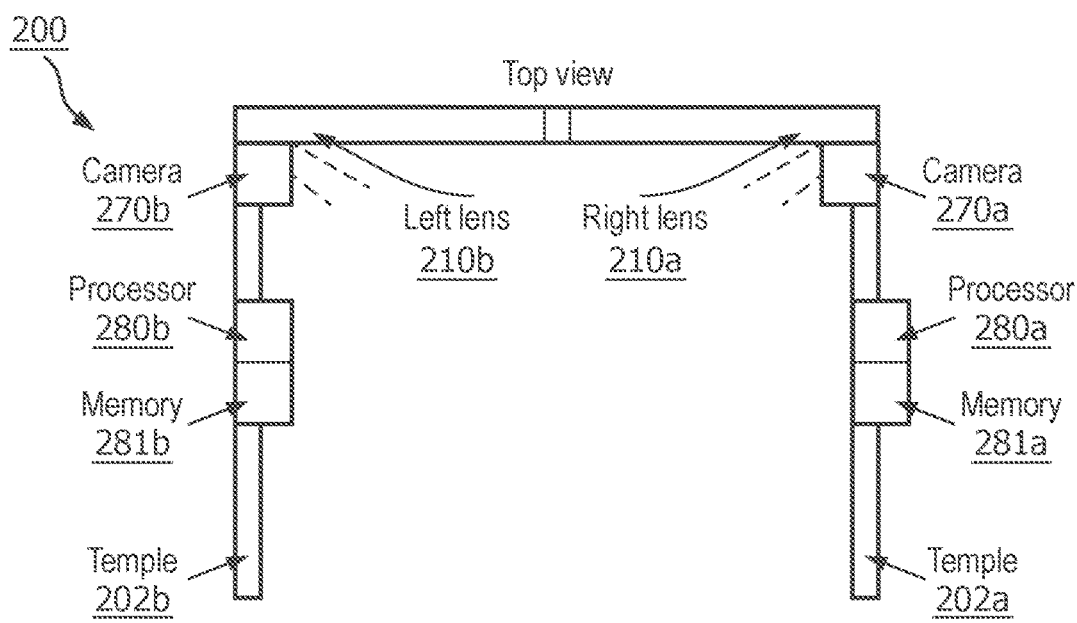
FIG. 2C illustrates a top view of a head-mountable device for a virtual cover for user interaction in augmented reality, in accordance with an aspect of the present disclosure.

FIG. 2C illustrates a top view of a head-mountable device for a virtual cover for user interaction in augmented reality, in accordance with an aspect of the present disclosure. In FIG. 2C, a variety of electronic elements are shown disposed along the right temple 202a and left temple 202b. The elements include a camera 270a along the right temple 202a, and a camera 270b along the left temple 202b. The left temple 202b also includes a processor 280b and a memory 281b, and the right temple 202a also includes a processor 280a and a memory 281a. The processors 280a, 280b and memories 281a, 281b are representative of elements of a general computer system which may be entirely or partially included in the head-mountable device 200.

The cameras 270a, 270b face rearward, and are used to capture eye movements of the subject wearing the head-mountable device 200. Though the cameras 270a, 270b are shown separate from the sensors 250 from FIG. 2A, the cameras 270a, 270b are consistent with a type of the sensors 250 in that they sense movement of the eyes of the subject wearing the head-mountable device 200.

The memories 281a, 281b store instructions and data for the head-mountable device 200, and the processors 280a, 280b execute the instructions for the head-mountable device 200. The instructions stored in memories 281a, 281b and executed by processors 280, 280b may include instructions for generating specific virtual objects to be superimposed in the field of view of the subject wearing the head-mountable device 200. the combination of the memory 281a and processor 280 may be considered a controller as described herein. Similarly, the combination of the memory 281b and the processor 280b may be considered a controller as described herein. Of course, the entirety of the head-mountable device 200 may be considered a controller as described herein.

Figure 3A:
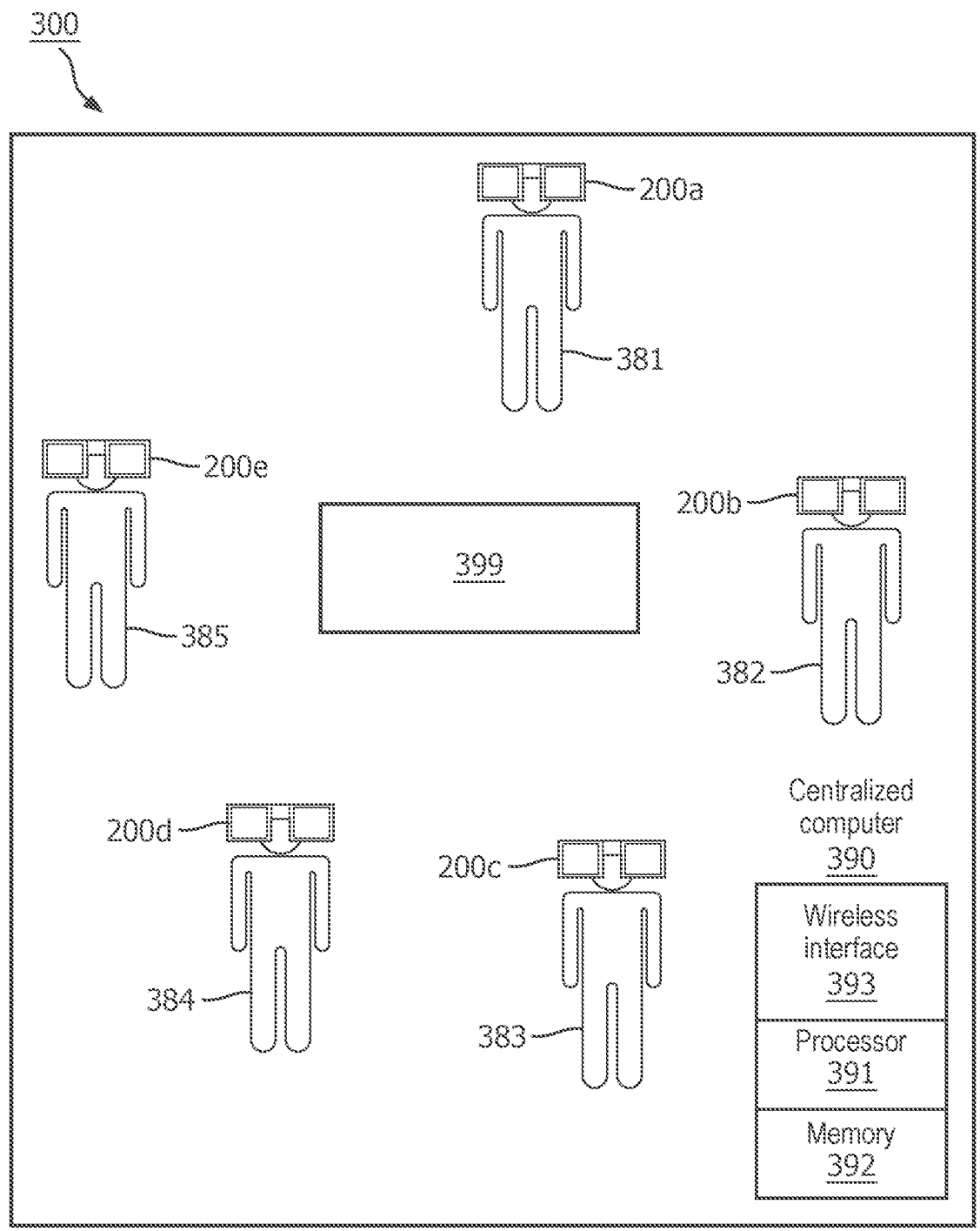
FIG. 3A illustrates a 3D space with subjects wearing head-mountable devices for a virtual cover for user interaction in augmented reality, in accordance with an aspect of the present disclosure.

FIG. 3A illustrates a space with subjects wearing head-mountable devices for a virtual cover for user interaction in augmented reality, in accordance with an aspect of the present disclosure. In FIG. 3A, five subjects 381-385 are shown disposed around a table 399 in the 3D space 300. Also in FIG. 3A, a centralized computer 390 is shown with a wireless interface 393, a processor 391 and a memory 392.

The embodiment of FIG. 3A is illustrative of the dangers of providing virtual operation members in a crowded and enclosed space. In the embodiment of FIG. 3A, the five subjects 381-385 may each be wearing head-mountable devices 200a-200e for augmented reality. If a virtual operation member is shown in a shared augmented reality space that is accessed by each of the five subjects 381-385, any of the five subjects may inadvertently activate the virtual operation member. Therefore, a cover or other enabling/disabling feature for a virtual operation member is provided to disable the virtual operation member when not in use. Additionally, power to enable the virtual operation member may be limited to fewer than all users, and may require authentication such as by a password.

The centralized computer 390 may be used to initially control the augmented reality such as by inputting settings for each virtual operation member and objects and/or virtual objects in the 3D space 300 that can be used to disable and enable each virtual operation member. Control of the 3D space may be passed to one of the five subjects 381-385 when a head-mountable device 200a-200e is activated. The passing of control may be according to predetermined instructions stored in the memory 392 and executed by the processor 391. The predetermined instructions for control of the 3D space 300 may allow one of the five subjects 381-385 or another subject in the 3D space 300 or outside of the 3D space 300 to change control of the 3D space.

The five subjects 381-385 include first subject 381, second subject 382, third subject 383, fourth subject 384 and fifth subject. First subject 381 is wearing a first head-mountable device 200a, the second subject 382 is wearing a second head-mountable device 200b, the third subject 383 is wearing a third head-mountable device 200c, the fourth subject 384 is wearing a fourth head-mountable device 200d, and the fifth subject 385 is wearing a fifth head-mountable device 200e. Each of the first head-mountable device 200a, second head-mountable device 200b, third head-mountable device 200c, fourth head-mountable device 200d and fifth head-mountable device 200e described herein may include any of the features specifically described with respect to the head-mountable device 200 shown in FIGS. 2A-2C. Additionally, each of the head-mountable devices 200a-200e may be wirelessly connected to each of the other head-mountable devices 200a-200e, as well as to the centralized computer 390. Each of the head-mountable devices 200a-200e may also be tethered to the centralized computer 390.

The 3D space 300 may be a room, such as an operating room in a hospital, and the five subjects 381-385 may be personnel such as medical personnel involved in a medical intervention for a patient disposed on the table 399. The teachings of the present disclosure are not limited to operating rooms or medical personnel, but for convenience this setting for the teachings herein may be repeatedly referenced.

In the operating room example, five subjects 381-385 may each have different responsibilities and rely on different information sources that provide different kinds of information. The five subjects 381-385 may also have responsibilities that rely on the same information source or information sources. As seen in FIG. 3A, it would be difficult to provide a common information source to the five subjects 381-385 via a single monitor since they are disposed around the table 399, and this would be particularly difficult for any personnel that are required to visually monitor a patient on the table 399 directly.

The 3D space 300 is an enclosure such as an operating room, and may be pre-mapped so that every physical object in the 3D space 300 is mapped in preparation for a virtual cover for user interaction in augmented reality described herein. The pre-mapping for the 3D space may be used therefore to provide each of the five subjects 381-385 with augmented reality. That is, the pre-mapping provides physical constraints that cannot be altered, whereas virtual objects can be provided in the 3D space in locations that do not conflict with the pre-mapped physical constraints.

In FIG. 3A, the head-mountable devices 200a-200e are used to provide a virtual cover for user interaction in augmented reality. Each head-mountable device 200 is configured to provide a transparent interface for the subject wearing the head-mountable device 200, so that when reality is not being augmented the subject is given an unaltered view of the physical world as seen through the head-mountable device 200. When reality is being augmented as described herein, the head-mountable device 200 is used to augment the view of the physical world with virtual objects superimposed in the view of the physical world.

Each of the subjects 281-285 may be provided dedicated unshared portions of the 3D space by the head-mountable devices 200a-200e. In other words, each of the head-mountable devices 200a-200e may uniquely provide a corresponding subject with a dedicated portion of the 3D space that will not appear in the view of the 3D space for another of the head-mountable devices 200a-200e. These dedicated portions shown in the view of only one of the five subjects 381-385 are described herein as unshared portions.

All the subjects 281-285 or subsets of the subjects 281-285 may also be provided access to a dedicated shared portion of the 3D space by the head-mountable devices 200a-2003. A virtual operation member may be provided individually to a user, such as an X-Ray technician, in an unshared portion of the 3D space, or may be provided to groups of users, such as multiple nurses, in a shared portion of the 3D space.

Figure 3B:
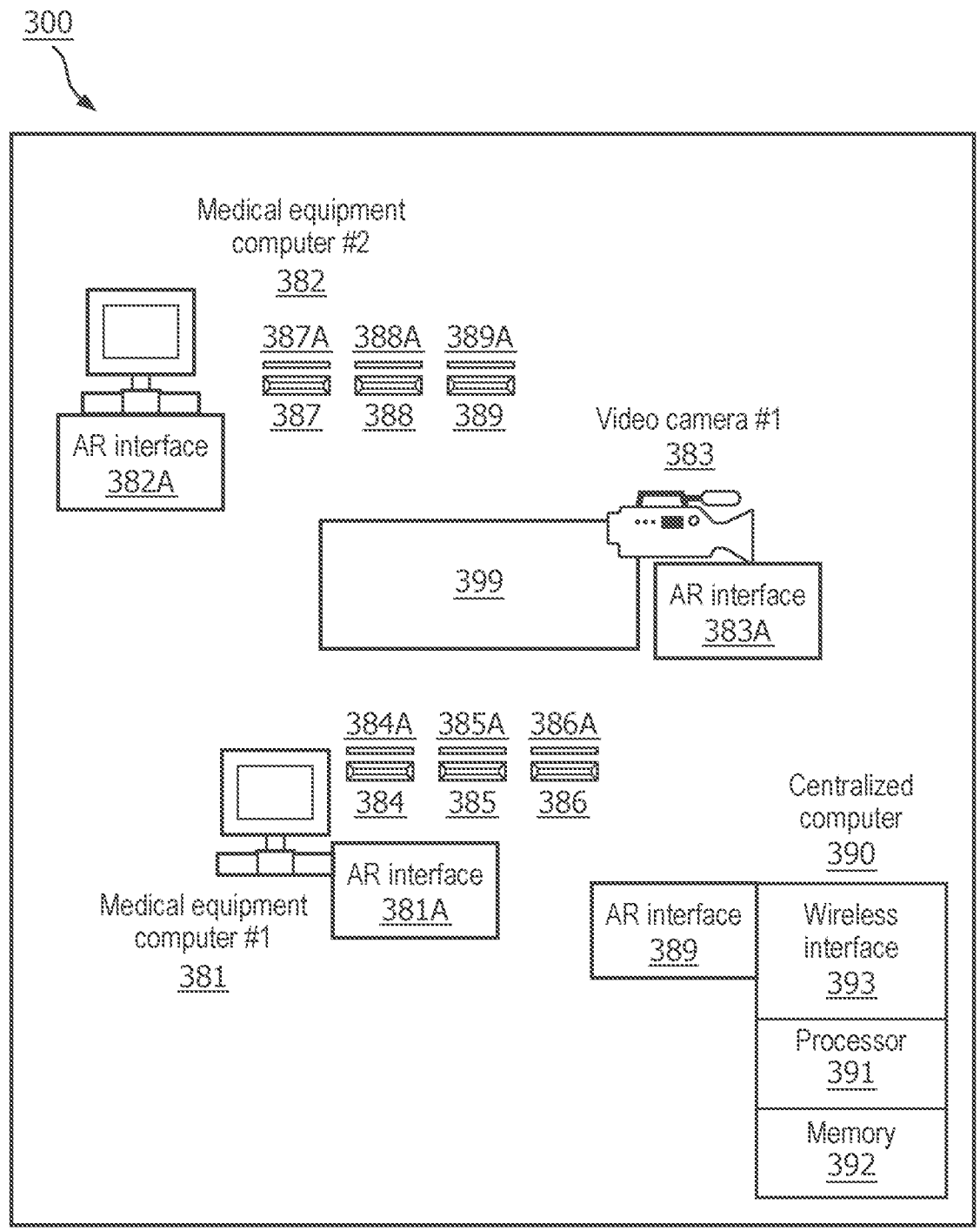
FIG. 3B illustrates another view of the 3D space in FIG. 3A with medical equipment provided with augmented reality interfaces and virtual operational members and virtual covers for user interaction in augmented reality, in accordance with an aspect of the present disclosure.

FIG. 3B illustrates another view of the 3D space in FIG. 3A with medical equipment provided with augmented reality interfaces for a virtual cover for user interaction in augmented reality, in accordance with an aspect of the present disclosure. In FIG. 3B, multiple different electronic devices are used to monitor and/or display medical information for a patient on the table 399.

A video camera #1 383 is used to provide a video feed of the patient during a medical intervention. An augmented reality interface 383A is used to selectively provide the video feed from video camera #1 383 to personnel via augmented reality.

A medical equipment computer #1 381 is used to obtain and display medical information from sensors on or around the patient. An augmented reality interface 381A is used to selectively provide the medical information to personnel via augmented reality. Additionally, three virtual operation members 384, 385 and 386 are provided for the medical equipment computer #1 381. Each of the three virtual operation members 384, 385 and 386 is covered with a corresponding virtual cover 384A, 385A and 386A.

A medical equipment computer #2 382 is also used to obtain and display medical information from sensors on or around the patient. An augmented reality interface 382A is used to selectively provide the medical information to personnel via augmented reality. Additionally, three virtual operation members 387, 388 and 389 are provided for the medical equipment computer #1 381. Each of the three virtual operation members 387, 388 and 389 is covered with a virtual cover 387A, 388A and 389A.

In the embodiment of FIGS. 3A and 3B, the virtual operation members 384-389 and virtual covers 394-399 are only visible via an augmented reality device configured to display the virtual operation members 384-389 and virtual covers 394-399. The software for such an augmented reality device must be authorized to display the virtual operation members 384-389 and virtual covers 394-399, to detect (virtual) interaction by any user with the virtual operation members 384-389 and virtual covers 394-399, and to use any detected virtual interaction to control either of the medical equipment computer #1 381 or medical equipment computer #2 382. In other words, users can be restricted from even seeing any of the virtual operation members 384-389 and virtual covers 394-399. Restricting unnecessary users from access to augmented reality features is another mechanism for avoiding inadvertent activation or control of the medical equipment computer #1 381 or medical equipment computer #2 382.

The centralized computer 390 is shown in FIG. 3B, and may be used to control, at least initially, the augmented reality provided via a shared portion of the 3D space 300. As noted, the centralized computer 390 includes a processor 391, memory 392, and a wireless interface 393. The centralized computer 390 may control both shared and unshared portion(s) of the 3D space by restricting an ability to view the shared portion(s), restricting an ability to alter the feeds provided via the shared portion(s), and restrict the ability to interact within the shared portion(s). Additionally, any data feeds from medical equipment computer #1 381 or medical equipment computer #2 382 or other equipment provided via an unshared or shared augmented reality screen may be routed through the centralized computer 390, or another centralized device, so that control of information provided via augmented reality in the 3D space 300 is implemented commonly at a single point, even if additional controls are implemented without the centralized computer 390 or other centralized device. The control provided by the centralized computer 390 may vary, such as when an authorized user switches control of shared portion(s) from the centralized computer 390 to another authorized user using, for example, a head-mountable device 200.

As an example of FIG. 3B, the 3D space 300 may be a sample room layout for an operating room used for a complex minimally-invasive structural heart procedure. In this procedure, multiple people in the room need to work to treat the patient. These people may include, for example:

An anesthesiologist to administer anesthesia and monitor the patient.

An echocardiographer to position a TEE probe and control ultrasound image acquisition.

An interventionalist #1 to navigates catheters, guidewires, and other devices to deliver therapy to the patient.

Interventionalists #2-3 to assist interventionalist #1.

A Nurse to bring appropriate tools and devices to the Interventionalists.

An X-ray technician to assist with operating an interventional x-ray system.

Examples of the information required for the people in the above example can include:

An intra-operative x-ray (live image, roadmaps, reference images)

An intra-operative ultrasound (TEE, ICE, IVUS, etc.)

Pre-operative imaging (Ultrasound, CT, MRI)

Patient historyPatient vitals, hemodynamics

Dose information (for staff—DoseAware, or patient)

Live views of what different people are seeing.

Overlays on live imaging

Targets/markers

In the example above, each of the people may use augmented reality and be provided with unshared and shared portions of the 3D space occupied by the augmented reality. Augmented reality interface 381A, augmented reality interface 382A, and augmented reality interface 383A may be used to provide the information to a shared portion of the 3D space that is visible using augmented reality. Using augmented reality can help avoid positioning multiple monitors throughout the 3D space and helps provide each authorized person using the shared augmented reality with a common perspective to observe the patient, the monitors, and each other, while also providing each authorized person using unshared augmented reality with information specific to their role.

Additionally, in the example above, a person may have access using augmented reality even when the person leaves the 3D space 300. For example, a nurse wearing a head-mountable device may leave the room to retrieve equipment and maintain communication and access to the first shared portion of the 3D space visible via augmented reality. The same access to the first shared portion can be provided for staff members sitting in an external control room, or senior staff members supervising junior staff members who may be called away to consult in a neighboring room.

Figure 4:
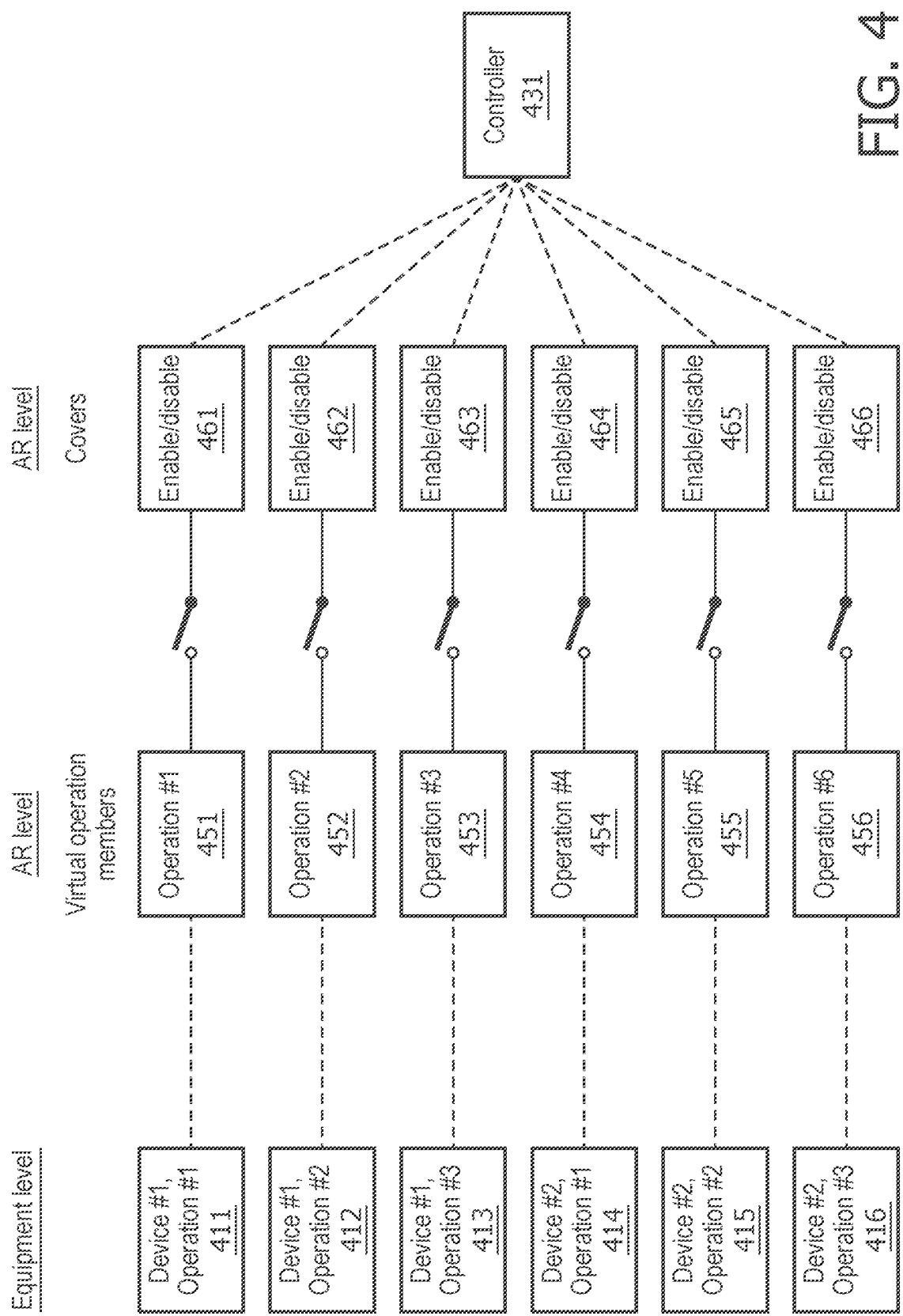
FIG. 4 illustrates a logical arrangement demonstrative of operational control of devices using a virtual cover for user interaction in augmented reality, in accordance with an aspect of the present disclosure.

FIG. 4 illustrates a logical arrangement demonstrative of operational control of devices using a virtual cover for user interaction in augmented reality, in accordance with an aspect of the present disclosure. In FIG. 4, the column on the left represents equipment controlled using augmented reality commands. The middle level represents the virtual operation members used to control individual operations of the equipment represented on the left. The right column represents the virtual covers provided to avoid inadvertent operation of the virtual operation members represented in the middle.

In FIG. 4, the column on the left includes two devices, i.e., device #1 and device #2. Each device has three operations associated/correlated with virtual operation members. Device #1, operation #1 411 is correlated with operation #1 451. Device #1, operation #2 412 is correlated with operation #2 452. Device #1, operation #3 413 is correlated with operation #3 453. Device #2, operation #1 414 is correlated with operation #4 454. Device #2, operation #2 415 is correlated with operation #5 455. Device #2, operation #3 416 is correlated with operation #6 456. The different operations in FIG. 4 may be operations such as, for example, on/off, focus and capture (e.g., for an image capturing device), refresh and update, or other forms of commands that can be input to different devices. The operations may also include be based on inputting values, such as by using a virtual dial or virtual keypad displayed in the augmented reality.

In FIG. 4, the covers are each shown as enable/disable boxes 461-466. Each virtual cover corresponds to a different virtual operation member and a different operation implemented by the different virtual operation members. A controller 431 may be implemented by any augmented reality device specifically authorized to access and interact with the covers and virtual operation members. For example, a supervisor in 3D space 300 may be provided with a headset designated to control the different covers for the rest of a team in the 3D space 300, so that any team member wishing to activate a protected operation must have the supervisor uncover the corresponding virtual operation member.

That is, as described above, at least two levels of control are required to operate equipment using virtual operation members. The first level is enabling control of the virtual operation members, such as by making the virtual operation members visible by uncovering a cover. The second level is to interact with the virtual operation members to activate the desired operation by the equipment.

Figure 5A:
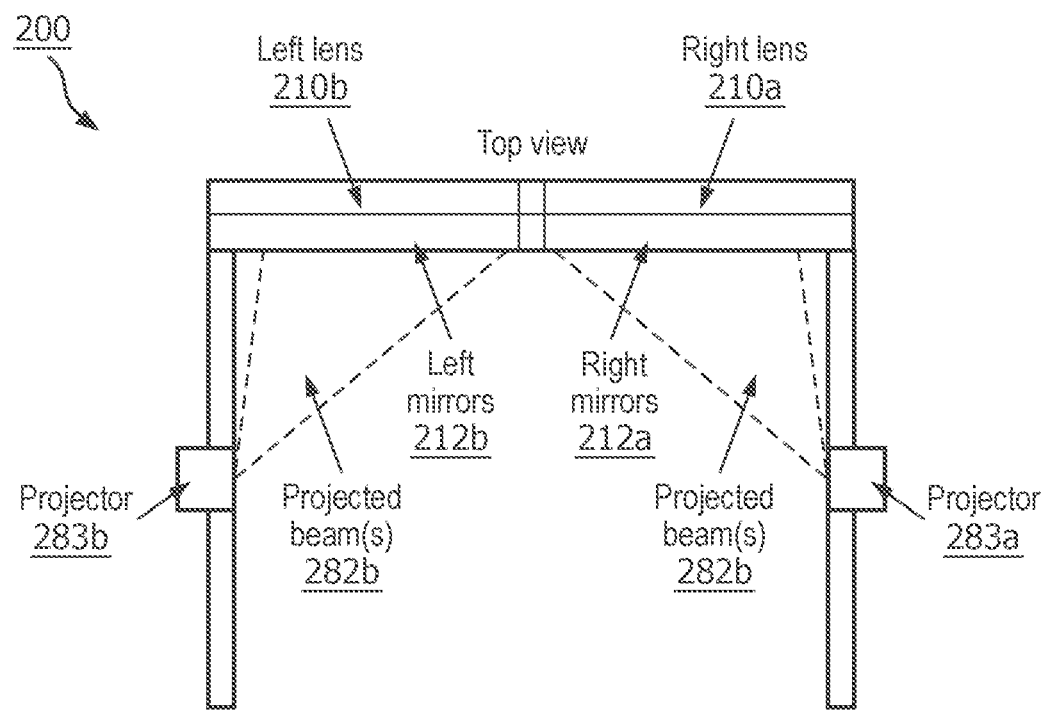
FIG. 5A illustrates a top view of another head-mountable device for a virtual cover for user interaction in augmented reality, in accordance with an aspect of the present disclosure.

FIG. 5A illustrates a top view of another head-mountable device for a virtual cover for user interaction in augmented reality, in accordance with an aspect of the present disclosure. In FIG. 5A, a combination of projector 283b and left mirrors 212b may form all or part of a display system. Similarly, a combination of projector 283a and right mirrors 212a may form all or part of a display system. The display systems work by the projectors 283a, 283b projecting light that is reflected by mirrors 212a, 212b into the eyes of the subject wearing the head-mountable device 200. The projectors 283a, 283b may operate together with the processors 280a, 280b from FIG. 2C to generate virtual objects superimposed in the view of the subject wearing the head-mountable device 200. The processors 280a, 280b may provide image data for each virtual object for the head-mountable device 200, and projectors 283a, 283b may project light for the left mirrors 212b and right mirrors 212a to reflect to display the images for each virtual object.

The mirrors 212a, 212b may be matrices of small mirrors arranged as a digital micromirror device DMD, for a digital light processing (DLP) projector. In any event, in FIG. 5A, the left mirrors 212b and the right mirrors 212a are transparent, so that when no light is reflected by the left mirrors 212b and the right mirrors 212a, the subject wearing the head-mountable device 200 will have a view of the unaltered physical world. However, the projectors 283a, 283b may, in operation, operate with the left mirrors 212b and the right mirrors 212a to generate the virtual objects that are superimposed in the field of view of the subject wearing the head-mountable device 200.

Figure 5B:
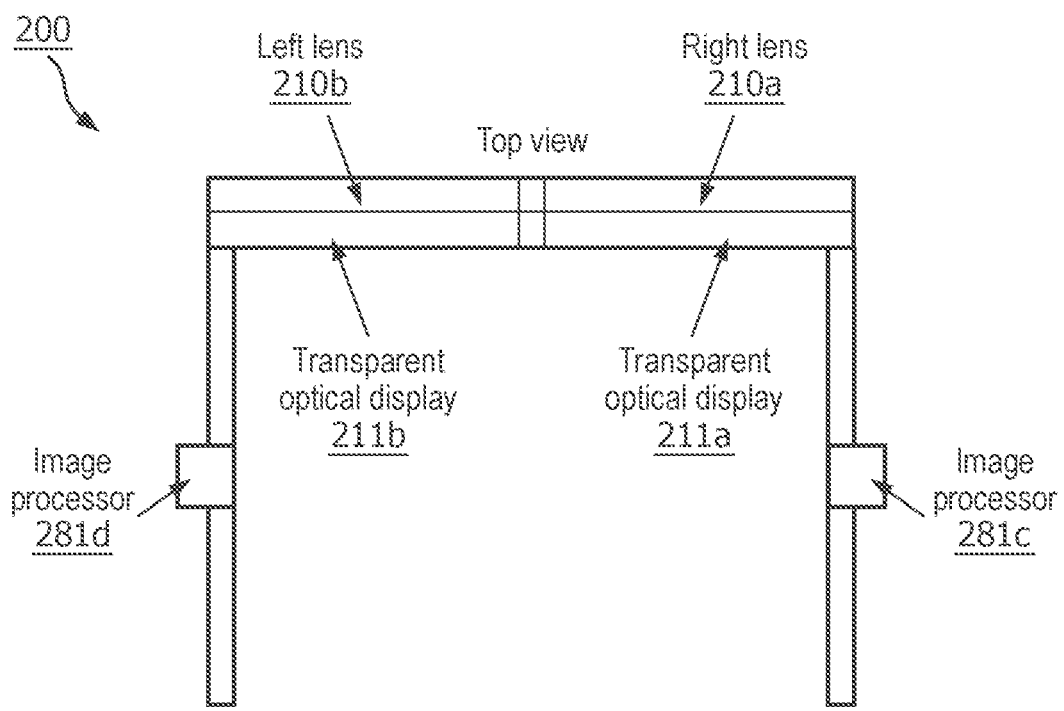
FIG. 5B illustrates a top view of another head-mountable device for a virtual cover for user interaction in augmented reality, in accordance with an aspect of the present disclosure.

FIG. 5B illustrates a top view of another head-mountable device for a virtual cover for user interaction in augmented reality, in accordance with an aspect of the present disclosure. In FIG. 5, a transparent optical display 211b is provided behind the left lens 210b, and a transparent optical display 211a is provided behind the right lens 210a. Image processor 281d controls elements of the transparent optical display 211b, and image processor 281c controls elements of the transparent optical display 211a.

In FIG. 5B, the combination of image processor 281d and transparent optical display 211b may form all or part of a display system. The combination of image processor 281c and transparent optical display 211a may form all or part of a display system. The image processors 281c, 281d may operate together with the processors 280a, 280b from FIG. 2 to generate virtual objects superimposed in the view of the subject wearing the head-mountable device 200. That is, the processors 280a, 280b may provide image data for each virtual object for the head-mountable device 200, and image processors 281c, 281d may control the individual elements of the transparent optical displays 211a, 211b to display the images for each virtual object.

The transparent optical displays 211a, 211b may, for example, simultaneously allow subjects to view the physical world and artificially generated virtual objects. The transparent optical displays 211a, 211b may include, for example, transparent and polarized OLEDs, light-guide optical elements, and similar materials arranged in a matrix that can be individually and logically controlled, i.e., without a projected beam as in FIG. 5A. Examples of the elements and materials that can be used for transparent optical displays 211a, 211b include an electroluminescent display elements, liquid crystal display (LCD) elements, and waveguides, reflective coatings.

FIGS. 5A and 5B show two examples of specific display systems that can be used to generate displays of virtual objects for augmented reality. It should be apparent that other types of display systems can be used to generate such displays of virtual objects consistent with the teachings of the present disclosure, and these two exemplary FIGs. are merely representative of mechanisms by which teachings herein can be implemented.

Figure 6:
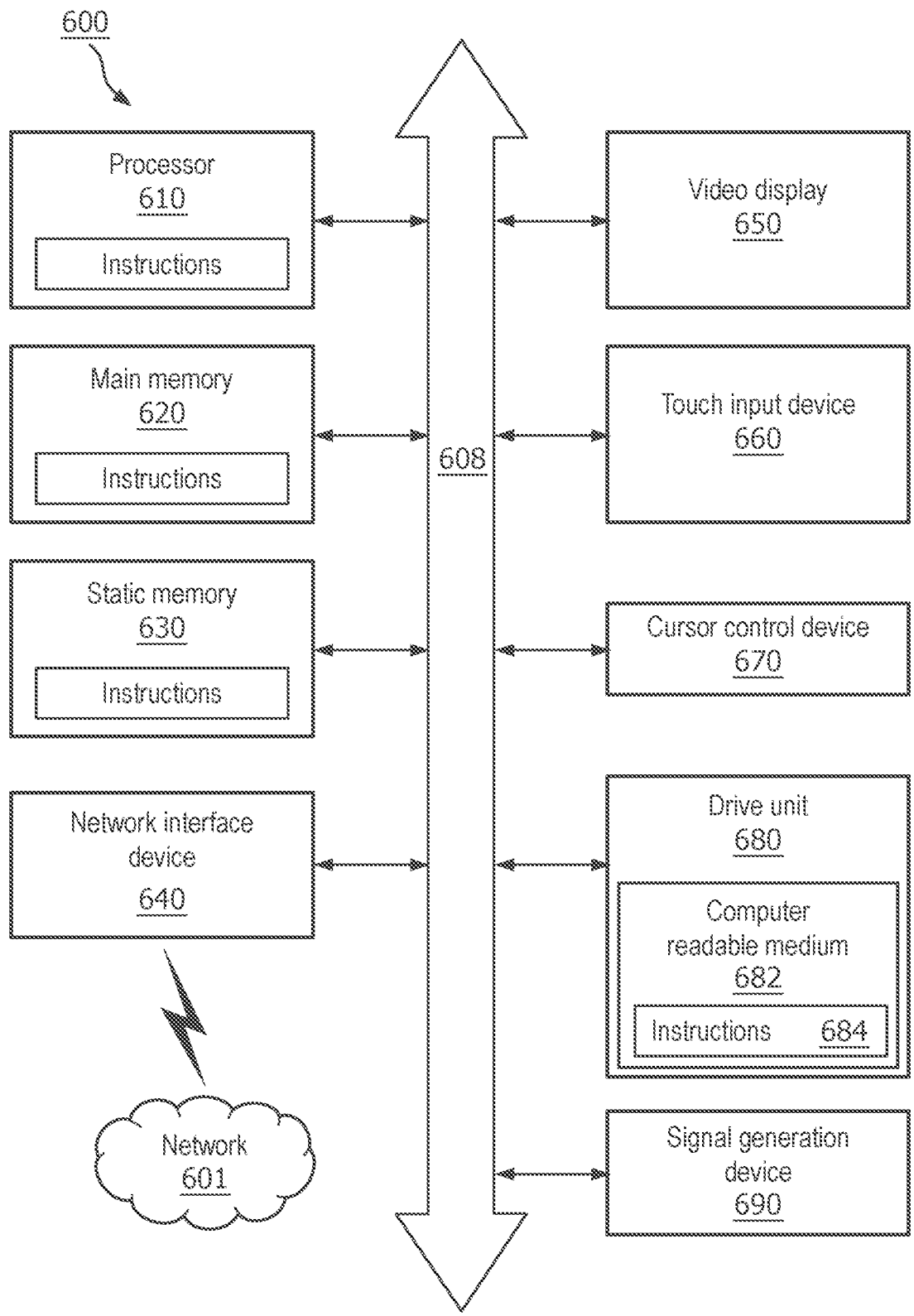
FIG. 6 illustrates an exemplary general computer system that includes a set of instructions for a virtual cover for user interaction in augmented reality, in accordance with an aspect of the present disclosure.

FIG. 6 is an illustrative embodiment of a general computer system 600, on which a method of a virtual cover for user interaction in augmented reality can be implemented. The computer system 600 can include a set of instructions that can be executed to cause the computer system 600 to perform any one or more of the methods or computer based functions disclosed herein. The computer system 600 may operate as a standalone device or may be connected, for example, using a network 603, to other computer systems or peripheral devices.

In a networked deployment, the computer system 600 may operate in the capacity of a server or as a client user computer in a server-client user network environment, or as a peer computer system in a peer-to-peer (or distributed) network environment. The computer system 600 can also be implemented as or incorporated into various devices, such as a head-mountable device, a stationary computer, a mobile computer, a personal computer (PC), a laptop computer, a tablet computer, a wireless smart phone, a personal digital assistant (PDA), a communications device, or any other machine capable of executing a set of instructions (sequential or otherwise) that specify actions to be taken by that machine. The computer system 600 can be incorporated as or in a device that in turn is in an integrated system that includes additional devices. In an embodiment, the computer system 600 can be implemented using electronic devices that provide voice, video or data communication. Further, while computer system 600 is individually illustrated, the term "system" shall also be taken to include any collection of systems or sub-systems that individually or jointly execute a set, or multiple sets, of instructions to perform one or more computer functions.

As illustrated in FIG. 6, the computer system 600 includes a processor 610. A processor for a computer system 600 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 600 is configured to execute software instructions to perform functions as described in the various embodiments herein. A processor for a computer system 600 may be a general-purpose processor or may be part of an application specific integrated circuit (ASIC). A processor for a computer system 600 may also be a microprocessor, a microcomputer, a processor chip, a controller, a microcontroller, a digital signal processor (DSP), a state machine, or a programmable logic device. A processor for a computer system 600 may also be a logical circuit, including a programmable gate array (PGA) such as a field programmable gate array (FPGA), or another type of circuit that includes discrete gate and/or transistor logic. A processor for a computer system 600 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 600 includes a main memory 620 and a static memory 630 that can communicate with each other via a bus 608. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 600 may further include a video display unit 650, such as a liquid crystal display (LCD), an organic light emitting diode (OLED), a flat panel display, a solid-state display, or a cathode ray tube (CRT). Additionally, the computer system 600 may include an input device 660, such as a keyboard/virtual keyboard or touch-sensitive input screen or speech and even voice input with speech and voice recognition, and a cursor control device 670, such as a mouse or touch-sensitive input screen or pad. The computer system 600 can also include a disk drive unit 680, a signal generation device 690, such as a speaker or remote control, and a network interface device 640. A computer system 600 may also include additional inputs (now shown) such as sensors that track poses (e.g., arm movement, eye movement, head movement) of one or more users in the environment around the computer system 600.

In an embodiment, as depicted in FIG. 6, the disk drive unit 680 may include a computer-readable medium 682 in which one or more sets of instructions 684, e.g. software, can be embedded. Sets of instructions 684 can be read from the computer-readable medium 682. Further, the instructions 684, when executed by a processor, can be used to perform one or more of the methods and processes as described herein. In an embodiment, the instructions 684 may reside completely, or at least partially, within the main memory 620, the static memory 630, and/or within the processor 610 during execution by the computer system 600.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 682 that includes instructions 684 or receives and executes instructions 684 responsive to a propagated signal; so that a device connected to a network 601 can communicate voice, video or data over the network 601. Further, the instructions 684 may be transmitted or received over the network 601 via the network interface device 640.

Figure 7:
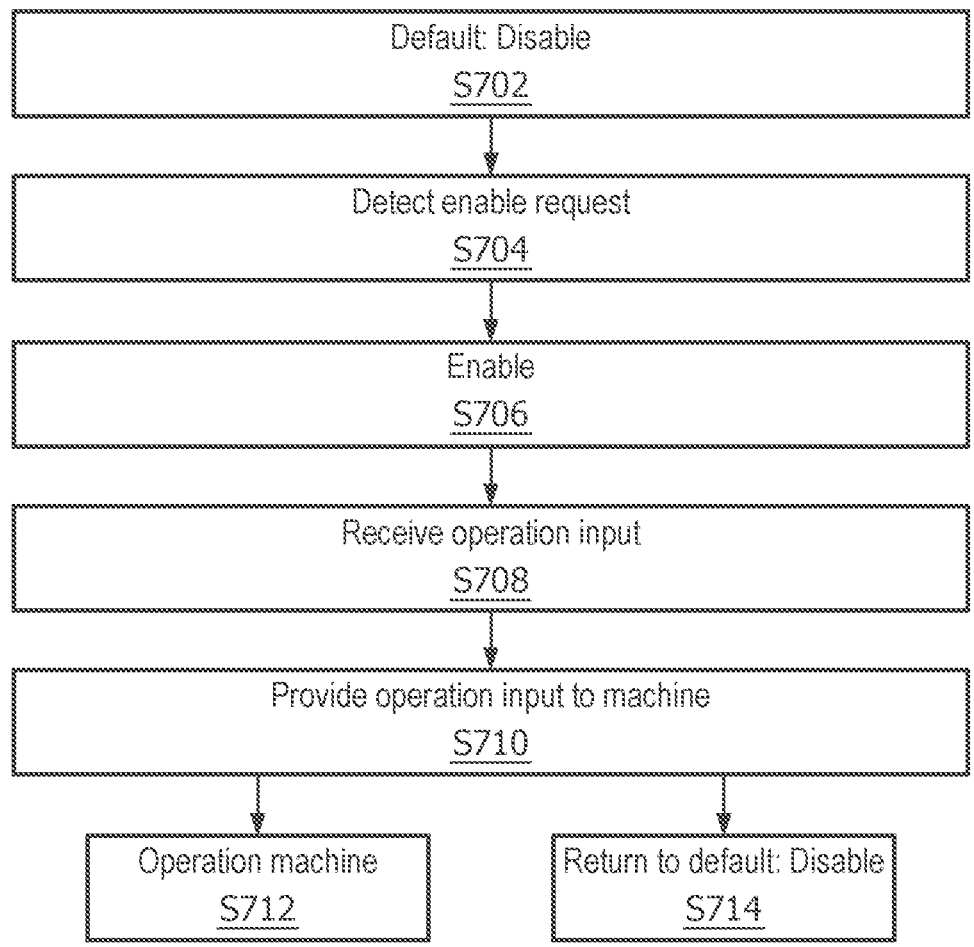
FIG. 7 illustrates another process for a virtual cover for user interaction in augmented reality, in accordance with an aspect of the present disclosure.

FIG. 7 illustrates another process for a virtual cover for user interaction in augmented reality, in accordance with an aspect of the present disclosure. In FIG. 7, the process starts at a default disabled state at S702. At S704, an enable request is detected. The enable request may be a swipe in a direction proximate to a virtual cover as recognized by sensors on an augmented reality device. Logic on the augmented reality device may interpret the gesture as a request to remove the cover, or otherwise enable the underlying virtual operation member.

At S706, the virtual operation member is enabled. At S708, operation input is received. The operation input may again be detected as interactive movement proximate to the virtual operation member, such as by pressing a virtual button or turning a virtual dial. At S710, the operation input is provided from the virtual operation member to the machine that is to be controlled. The operation input may be provided over a wireless interface to a machine controller that controls the machine using received commands from augmented reality devices.

At S712, the machine is operated in accordance with the command, and simultaneously at S714 the virtual operation member returns to the default disabled state, such as by closing the virtual cover and removing the virtual operation member from sight. As noted previously, the process described herein may involve coordinating an augmented reality device with a separate machine.

Figure 8:
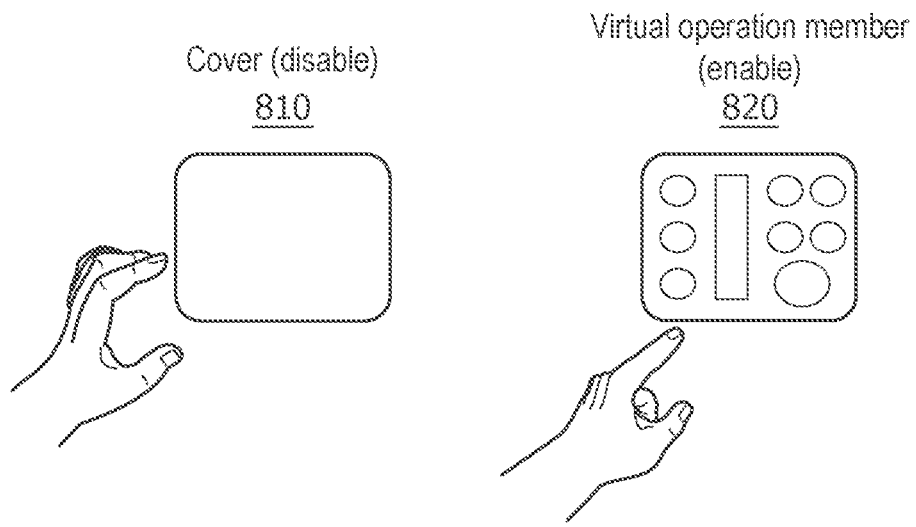
FIG. 8 illustrates another process for a virtual cover for user interaction in augmented reality, in accordance with a representative embodiment.

FIG. 8 illustrates another process for a virtual cover for user interaction in augmented reality, in accordance with a representative embodiment. In FIG. 8, virtual buttons have a virtual cover masking interaction with them until a specific gesture enables their display and functionality. Movement of a user's hand to perform the gesture is detected using sensors on the augmented reality device, and the underlying virtual operation member with the 8 buttons and 1 bar is revealed so that interaction is enabled.

An example of use for a virtual cover for user interaction in augmented reality is for an interventional x-ray system control with a head-mounted augmented reality display device. The user wears the head-mounted augmented reality display device. Virtual buttons for control of the X-ray system can be placed by the user anywhere in the 3D space except where physical objects already exist. The virtual buttons are masked on the left side of FIG. 8, until unlocked/unmasked by a specific gesture recognized by the head-mounted augmented reality display device. At this point, the user is free to interact with the virtual buttons to control the interventional x-ray system as in FIG. 8 on the right. (FIG. 1, right). As an example, the virtual buttons may be used to move a c-arm to a new angle. Even if the virtual cover does not return to the disabled state automatically, the user is able to mask the virtual buttons with another gesture recognized by the head-mounted augmented reality display device.

Another example of a use for a virtual cover for user interaction in augmented reality is for an interventional x-ray system control with a projection. In this example, virtual buttons can be projected onto an X-ray detector. The virtual buttons are masked until a foot pedal of the X-ray system is depressed, resulting in the virtual buttons being unmasked and enabled. The user can then interact with the virtual buttons in the augmented reality to control the interventional X-ray system. For example, the user may interact with the virtual buttons to move the X-ray detector up and down. When the user wants to mask the buttons again, the foot pedal is released. In this example, the enable/disable function is implemented using a physical component (the foot pedal), and enables use of the virtual operation member (virtual buttons), which in turn are used to control the physical system (interventional X-ray system). Thus, the augmented reality system used by the user must coordinate with the physical components of the foot pedal and the X-ray system. As yet another example of a use for a virtual cover for user interaction in augmented reality, a robotic system (e.g., a surgical robotic system) may be controlled with a head-mounted augmented reality display device. In this example, the user wears a head-mounted augmented reality display device. The virtual button is in the form of a virtual object that can be moved around by the user in augmented reality. For example, the virtual button may be moved in augmented reality to designate the insertion point of a drill for pedicle screw placement. In this example, the virtual button cannot be moved until the user positions a cursor onto a target on a tool using their head, i.e., by positioning their head to move the cursor onto the target. This unmasks the virtual object for repositioning. As the tool is repositioned the robot follows the movement. To disable the positioning, the user moves the cursor off the target by again repositioning his/her head. An example of such integrated use of augmented reality and physical reality is shown in FIGS. 9 and 9B.

Figure 9A:
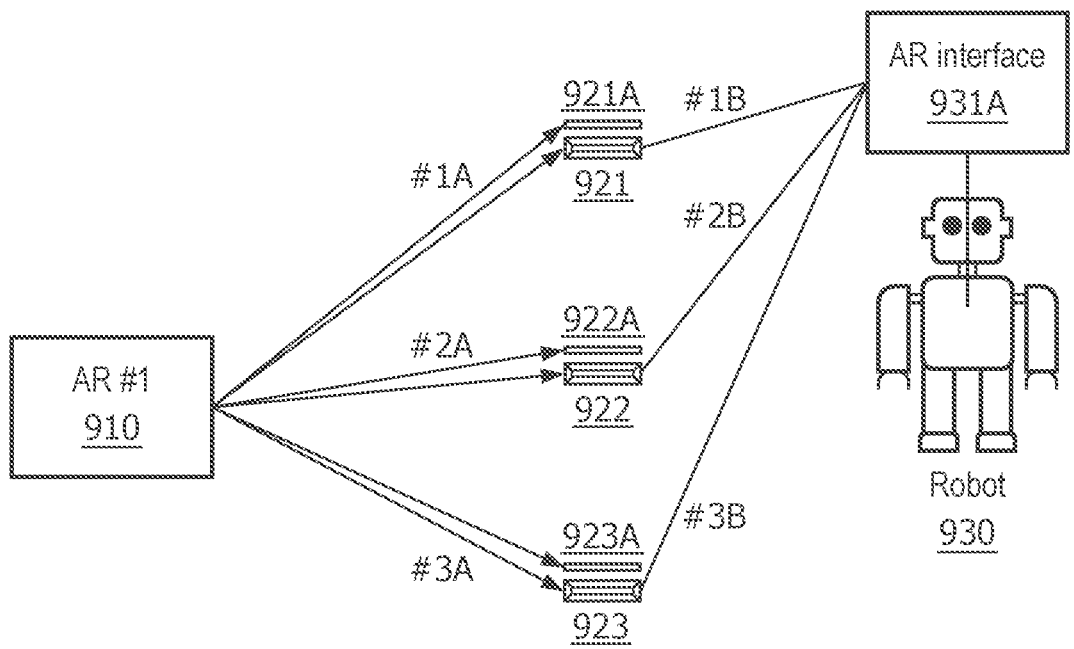
FIG. 9A illustrates an embodiment of enabling a virtual operation member using a virtual cover for user interaction, in accordance with a representative embodiment.

FIG. 9A illustrates an embodiment of enabling a virtual operation member using a virtual cover for user interaction, in accordance with a representative embodiment. In FIG. 9A, an augmented reality device #1 910 displays the virtual covers 921*a*, 922A, 923A virtually covering virtual operational members 921, 922, 923. The display implemented by augmented reality device #1 910 may dynamically change based on the viewpoint of the augmented reality device #1 910, and virtual objects such as the various covers and operational members may correspond to specific locations and spaces within a 3D space that is mapped. That is, the various covers and operational members may appear only to an augmented reality device with a view into particular spaces inside the 3D space.

In FIG. 9A, a robot 930 is controllable via the virtual operational members 921, 922, 923 and an augmented reality interface 931A. The robot 930 may be a surgical robot, such as a commercial surgical robot that is used to perform surgeries on a patient. The augmented reality interface 931A may correspond specifically to the robot 930, or may correspond to a set of machines such as the robot 930. In operational step #1A, the augmented reality device #1 910 removes the virtual cover 921A, and interacts with virtual operational member 921. For example, at operational step #1A, the virtual operational member 921 may correspond to turning the robot 930 on or off. At operational step #1B, the interaction with the virtual operational member 921 is detected, and results in an instruction being sent to the augmented reality interface 931A to turn the robot on or off. In operational step #2A, the augmented reality device #1 910 removes the virtual cover 922A, and interacts with virtual operational member 922. For example, at operational step #2A, the virtual operational member 922 may correspond to turning the robot 930 to the left or the right. In operational step #2B, the interaction with the virtual operational member 922 is detected, and results in an instruction being sent to the augmented reality interface 931A to move to the left or right. In operational step #3A, the augmented reality device #1 910 removes the virtual cover 923A, and interacts with virtual operational member 923. For example, at operational step #3A, the virtual operational member 923 may correspond to the robot 930 lifting an arm up or down. In operational step #3B, the interaction with the virtual operational member 923 is detected, and results in an instruction being sent to the augmented reality interface 931A to move the robot arm up or down. In an embodiment, the robot 930 may be controlled over a communications network from a remote source that has access to the augmented reality in the 3D space that includes the robot 930.

Figure 9B:
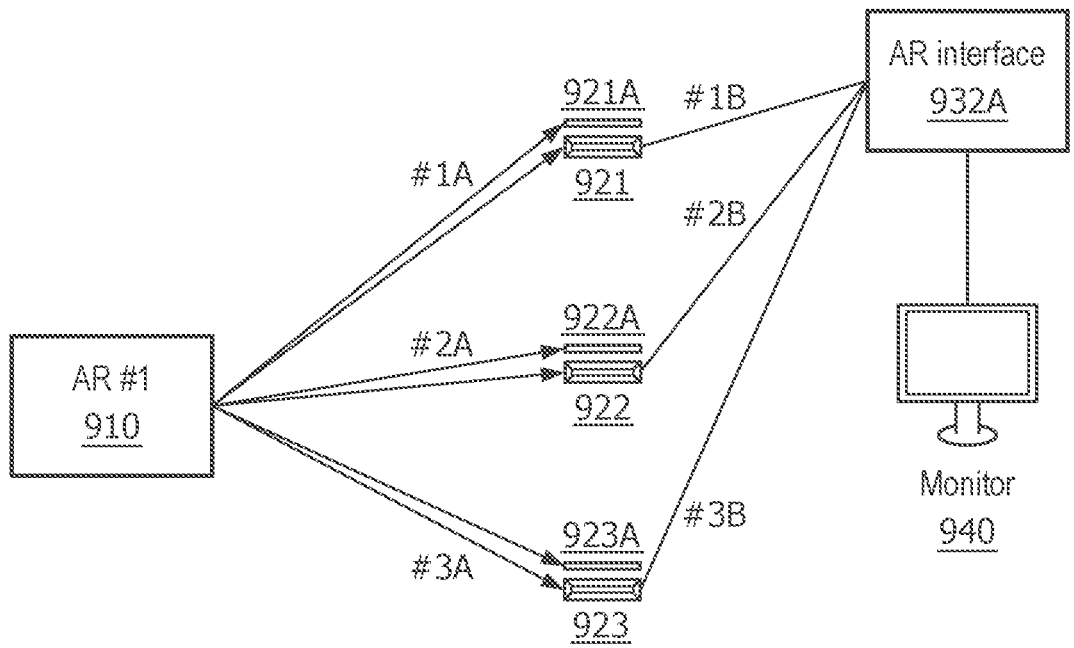
FIG. 9B illustrates another embodiment of enabling a virtual operation member to control operation of a machine in a 3D space, in accordance with a representative embodiment.

FIG. 9B illustrates another embodiment of enabling a virtual operation member to control operation of a machine in a 3D space, in accordance with a representative embodiment. In FIG. 9A, an augmented reality device #1 910 again displays the virtual covers 921*a*, 922A, 923A virtually covering virtual operational members 921, 922, 923. The display implemented by augmented reality device #1 910 may again dynamically change based on the viewpoint of the augmented reality device #1 910, and virtual objects such as the various covers and operational members may correspond to specific locations and spaces within a 3D space that is mapped. That is, the various covers and operational members may appear only to an augmented reality device with a view into particular spaces inside the 3D space.

In FIG. 9B, a monitor 940 is controllable via the virtual operational members 921, 922, 923 and an augmented reality interface 932A. The augmented reality interface 932A may correspond specifically to the monitor 940, or may correspond to a set of machines such as the monitor 940 930. In operational step #1A, the augmented reality device #1 910 removes the virtual cover 921A, and interacts with virtual operational member 921. For example, at operational step #1A, the virtual operational member 921 may correspond to turning the monitor 940 on or off. At operational step #1B, the interaction with the virtual operational member 921 is detected, and results in an instruction being sent to the augmented reality interface 931A to turn the monitor on or off. In operational step #2A, the augmented reality device #1 910 removes the virtual cover 922A, and interacts with virtual operational member 922. For example, at operational step #2A, the virtual operational member 922 may correspond to the monitor 940 generating a display from a particular source. In operational step #2B, the interaction with the virtual operational member 922 is detected, and results in an instruction being sent to the augmented reality interface 931A to tune to the particular source. In operational step #3A, the augmented reality device #1 910 removes the virtual cover 923A, and interacts with virtual operational member 923. For example, at operational step #3A, the virtual operational member 923 may correspond to the monitor 940 turning volume from the particular source up or down. In operational step #3B, the interaction with the virtual operational member 923 is detected, and results in an instruction being sent to the augmented reality interface 931A to turn the volume on the monitor 940 up or down.

In an alternative example, the tool is repositioned virtually until a final position is achieved. Afterwards the user enables the robot to move to the position by moving a cursor, again by positioning their head, to a target on the virtual tool (or on the robot, or somewhere else in the room).

As described above, a variety of forms of input can be detected by an augmented reality device or by a physical device, and used to enable a virtual operation member provided via augmented reality. The virtual operation member will only be visible using a device capable of receiving and authorized to receive data/information to display the virtual operation member, so the virtual cover and the virtual operation member may be restricted from all but an authorized augmented reality device. Additionally, the virtual operation member is used to operate a physical device, such as a medical machine used to monitor or otherwise assist in a medical intervention. Accordingly, input to the virtual operation member is detected by the authorized augmented reality device, and then provided to the physical device to control the physical device. The coordinate between the virtual operation member and the physical device may be provided via separate software programs stored in memories and executed separately by different processors.

Accordingly, a controller for controlling the virtual cover may be considered a combination of memory that stores instructions and a processor that executed the instructions, to detect user instructions to enable a virtual operation member and then to uncover and enable the virtual operation member for use. When the enable/disable functions are provided by a physical object such as a foot pedal, the controller for controlling the virtual cover may be the memory and processor combination, and may execute instructions to receive user instructions (via the foot pedal) to enable the virtual operation member and then to uncover and enable the virtual operation member for use. In either case, the controller that detects manipulation of the virtual operation member coordinates with the machine to be controlled by providing the instructions interpreted by the controller to the machine to be controlled.

Accordingly, a virtual cover for user interaction in augmented reality enables multiple different levels of protection when virtual operation members are used to control a machine. The controller can detect user instructions, enable and disable the virtual operation member, and even hide or otherwise obscure the virtual operation member from view unless a specific user interaction or instruction is detected.

Though a variety of embodiments are shown herein using augmented reality headsets, augmented reality controllers for a shared portion of a 3D space can also be provided to a centralize computer 390 in the 3D space, or even remote computers. The controllers will typically include a minimum of memories that store instructions and processors that execute the instructions, but may include other components or subcomponents.

Additionally, while aspects of the control are described as being preplanned for augmented reality sessions, control may be dynamically initiated or changed during an augmented reality session. For example, an authorized user may simply state that a virtual operation member should be hidden or moved to a corner (upper right, upper left, lower right, lower left) to avoid inadvertent interaction. In an embodiment, such a dynamic instruction from an authorized user can be detected, accepted and obeyed by an augmented reality device, and then fed back to all other augmented reality devices that share access to the same virtual operation member and the same shared space. In this way, a change in the display of one user in a shared environment can be made to the display of all other users instantly, either through a central controller or by directly communicating with the other augmented reality devices such as by a local wireless signal.

Although a virtual cover for user interaction in augmented reality has been described with reference to several exemplary embodiments, it is understood that the words that have been used are words of description and illustration, rather than words of limitation. Changes may be made within the purview of the appended claims, as presently stated and as amended, without departing from the scope and spirit of a virtual cover for user interaction in augmented reality in its aspects. Although a virtual cover for user interaction in augmented reality has been described with reference to particular means, materials and embodiments, a virtual cover for user interaction in augmented reality is not intended to be limited to the particulars disclosed; rather a virtual cover for user interaction in augmented reality extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

According to an aspect of the present disclosure, a controller for augmenting reality in a 3D space includes a memory that stores instructions, and a processor that executes the instructions. The controller controls a display system configured to present virtual objects in the 3D space. When executed by the processor, the instructions cause the controller to perform a process including detecting a first action by a user relative to an object or a virtual object in the 3D space, and selectively enabling or disabling a virtual operation member based on detecting the first action between the user and the object or virtual object in the 3D space. The virtual operational member is configured, when operated, to control operation of a machine in the 3D space.

According to another aspect of the present disclosure, the virtual object in the 3D space comprises a virtual cover for the virtual operational member. The first action comprises a first interaction when the user closes the virtual cover over the virtual operational member. According to yet another aspect of the present disclosure, the object in the 3D space comprises a physical object. The first action comprises a first interaction when the user depresses the physical object in the 3D space.

According to still another aspect of the present disclosure, the first action comprises a voice command from the user.

According to another aspect of the present disclosure, the first action comprises a first interaction when the user makes a gesture in the 3D space.

According to yet another aspect of the present disclosure, the first action comprises positioning of a head of the user in the 3D space.

According to still another aspect of the present disclosure, the action comprises positioning of eyes of the user in the 3D space.

According to another aspect of the present disclosure, the virtual operational member is selectively placed at a location in the 3D space.

According to yet another aspect of the present disclosure, the virtual operational member comprises a virtual button.

According to still another aspect of the present disclosure, the virtual operational member comprises a directional controller configured to control a direction of movement of an object in the 3D space.

According to another aspect of the present disclosure, the virtual operation member is projected onto an object in the 3D space.

According to yet another aspect of the present disclosure, when the virtual operational member is selectively disabled by the first action, the virtual operational member is configured to be selectively enabled based on the controller detecting a second interaction between the user and the object or the virtual object in the 3D space. When the virtual operational member is selectively enabled by the first action, the virtual operational member is configured to be selectively disabled based on the controller detecting a second interaction between the user and the object or the virtual object in the 3D space According to still another aspect of the present disclosure, the display system is configured to project a virtual cursor in the 3D space from the controller, and the first action comprises the user moving the cursor onto a target.

According to another aspect of the present disclosure, the virtual operational member corresponds to a physical operational member, and the physical operational member is moved to a position of the virtual operation member based on the processor detecting the first action. According to yet another aspect of the present disclosure, the wherein the machine comprises a display device and the control includes controlling the display device to display or not display content.

According to still another aspect of the present disclosure, the 3D space is based on a pre-defined physical environment on which the virtual objects are superimposed by the display system.

According to another aspect of the present disclosure, the controller comprises a head-mountable display, and the 3D space is a space in which the user wears the head-mountable display.

According to an aspect of the present disclosure, a method for controlling features in a 3D space with augmented reality includes controlling a display system configured to present virtual objects in the 3D space. The method also includes detecting a first action by a user relative to an object or a virtual object in the 3D space. The method further includes selectively enabling or disabling a virtual operation member based on detecting the first action between the user and the object or virtual object in the 3D space. The virtual operational member is configured, when operated, to selectively control a controllable item in the 3D space.

According to another aspect of the present disclosure, the method includes detecting a second action by the user; and moving the virtual operational member based on the second action by the user.

According to another aspect of the present disclosure, the method includes covering the virtual operation member with the virtual object in the 3D space based on detecting the first action by the user.

One or more embodiments of the disclosure may be referred to herein, individually and/or collectively, by the term "invention" merely for convenience and without intending to voluntarily limit the scope of this application to any specific invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment to streamline the disclosure. This disclosure is not to be interpreted as reflecting an intention that the claimed embodiments require more features than are expressly recited in each claim. Rather, as the following claims reflect, inventive subject matter may be directed to less than all features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for controlling an operation based on user interaction in an augmented reality space, the controller comprising:
a processor configured to:
control display of a virtual operational member in the augmented reality space viewed relative to a 3D physical space, wherein the virtual operational member is configured to control an operation of equipment in the 3D physical space;
detect an action, by a user, relative to a virtual cover in the augmented reality space; and
position the virtual cover to hide or unhide the virtual operational member in the augmented reality space based on the detected action; and
enable or disable the operation of the equipment in the 3D physical space based on the position of the virtual cover in the augmented reality space.

2. The controller of claim 1, wherein the detected action comprises opening or closing the virtual cover over the virtual operational member in the augmented reality space.

3. The controller of claim 1, wherein the detected action comprises an interaction in which the user provides a voice command.

4. The controller of claim 1, wherein the detected action comprises an interaction in which the user makes a gesture in the 3D physical space.

5. The controller of claim 1, wherein the detected action comprises an interaction in which the user positions the user's head in the 3D physical space.

6. The controller of claim 1, wherein the detected action comprises an interaction in which the user positions the user's eyes in the 3D physical space.

7. The controller of claim 1, wherein the processor is further configured to place the virtual operational member at a location in the augmented reality space relative to the 3D physical space.

8. The controller of claim 1, wherein the virtual operational member comprises a virtual button.

9. The controller of claim 1, wherein the virtual operational member comprises a directional controller configured to control a direction of movement of a physical object in the 3D physical space.

10. The controller of claim 1, wherein the virtual operational member is projected onto a physical object in the 3D physical space.

11. The controller of claim 1, wherein:
if the virtual operational member is hidden by the action, the processor is configured to unhide the virtual operational member based on detection of a second action by the user relative to the virtual cover in the augmented reality space, and
if the virtual operational member is unhidden by the action, the processor is configured to hide the virtual operational member based on detection of a second action by the user relative to the virtual cover in the augmented reality space.

12. The controller of claim 1, wherein the virtual operational member corresponds to a physical operational member, and the physical operational member is moved to a position of the virtual operational member based on detection of the action.

13. The controller of claim 1, wherein the virtual operational member is configured to control an operation of a medical machine in the 3D physical space.

14. The controller of claim 1, wherein the processor is further configured to:
determine one or more users that are authorized to perform the operation; and
cause the virtual operational member and the virtual cover to be made visible to the one or more users.

15. The controller of claim 1, wherein the 3D space includes a pre-defined physical environment on which the augmented reality space with the virtual operational member and virtual cover is superimposed by a display system.

16. The controller of claim 1, further comprising a display system that includes a head-mountable display configured to display the augmented reality space relative to the 3D physical space.

17. A method for controlling an operation based on user interaction in an augmented reality space, the method comprising:
controlling display of a virtual operational member in the augmented reality space viewed relative to a 3D physical space, wherein the virtual operational member is configured to control an operation of equipment in the 3D physical space;
detecting an action, by a user, relative to a virtual cover in the augmented reality space;
positioning the virtual cover to hide or unhide the virtual operational member in the augmented reality space based on the detected action; and
enabling or disabling the operation of the equipment in the 3D physical space based on position of the virtual cover in the augmented reality space.

18. The method of claim 17, wherein the detected action comprises opening or closing the virtual cover over the virtual operational member in the augmented reality space.

19. The method of claim 17, wherein the virtual operational member is configured to control an operation of a medical machine in the 3D physical space.

20. The method of claim 17, further comprising:
determining one or more users that are authorized to perform the operation; and
causing the virtual operational member and the virtual cover to be made visible to the one or more users.

* * * * *